United States Patent [19]

Leif

[11] 4,258,316
[45] Mar. 24, 1981

[54] USE OF FLUID RETARDING ION CONDUCTING MATERIAL

[75] Inventor: Robert C. Leif, Coral Gables, Fla.

[73] Assignee: Coulter Electronics, Inc., Hialeah, Fla.

[21] Appl. No.: 967,773

[22] Filed: Dec. 8, 1978

[51] Int. Cl.³ .......................................... G01N 27/00
[52] U.S. Cl. ............................... 324/71 CP; 324/453; 324/466
[58] Field of Search .................. 324/438, 71 CP, 425, 324/453, 466; 356/72

[56] References Cited

U.S. PATENT DOCUMENTS

| | | | |
|---|---|---|---|
| 2,382,734 | 8/1945 | Marks | 324/438 |
| 3,131,348 | 4/1964 | Taylor et al. | 324/438 |
| 3,159,783 | 12/1964 | Sparnaay | 324/438 |
| 3,258,683 | 6/1966 | Lawrence | 324/466 |
| 3,440,525 | 4/1969 | Cardeiro | 324/438 |

*Primary Examiner*—Michael J. Tokar
*Attorney, Agent, or Firm*—William A. Newton

[57] ABSTRACT

An improved particle sensing transducer apparatus and method for studying the physical properties of particles suspended in an electrolyte solution. The transducer apparatus includes a first chamber, at least a portion of which contains a quantity of the electrolyte solution with a first electrode disposed therein. A second chamber is provided, at least a portion of which contains a quantity of the electrolyte solution with a second electrode disposed therein. The transducer further includes an orifice for establishing a constricted electrical path by providing a passageway for a sample flow of electrolyte solution containing the particles between the two chambers. The improvement comprises a fluid retarding, ion conducting material, such as a gel, frit or membrane, interposed between the sample flow and at least one of the electrodes so as to pass an ionic current while retarding the electrolyte flow from the electrode.

18 Claims, 4 Drawing Figures

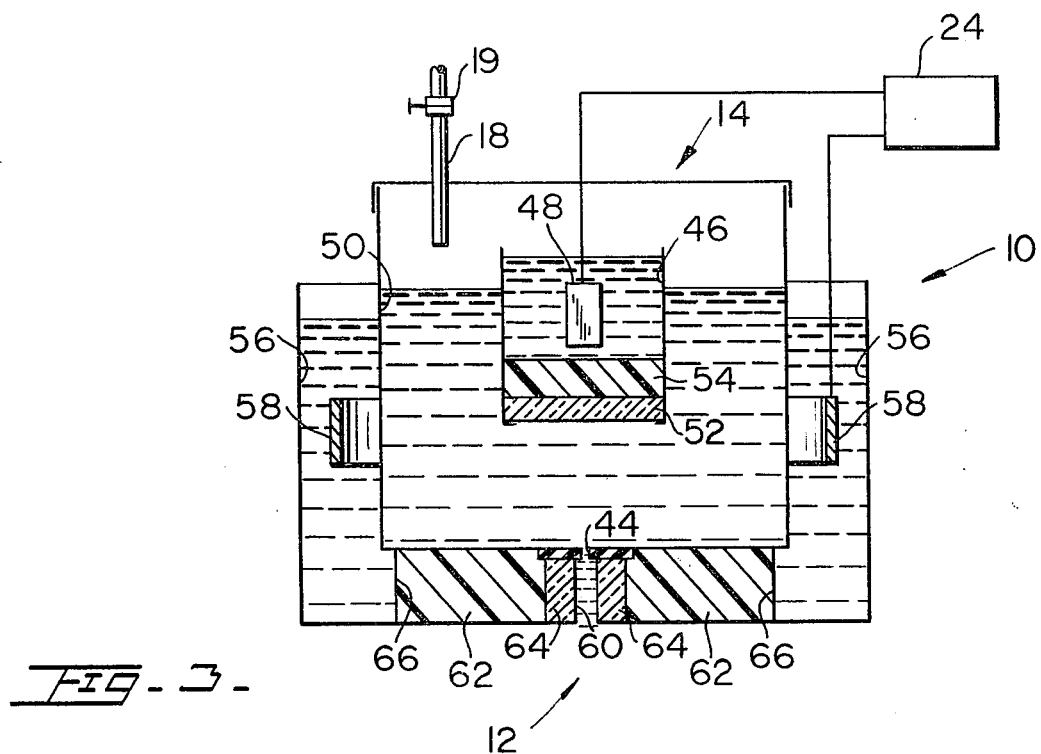
FIG-3-
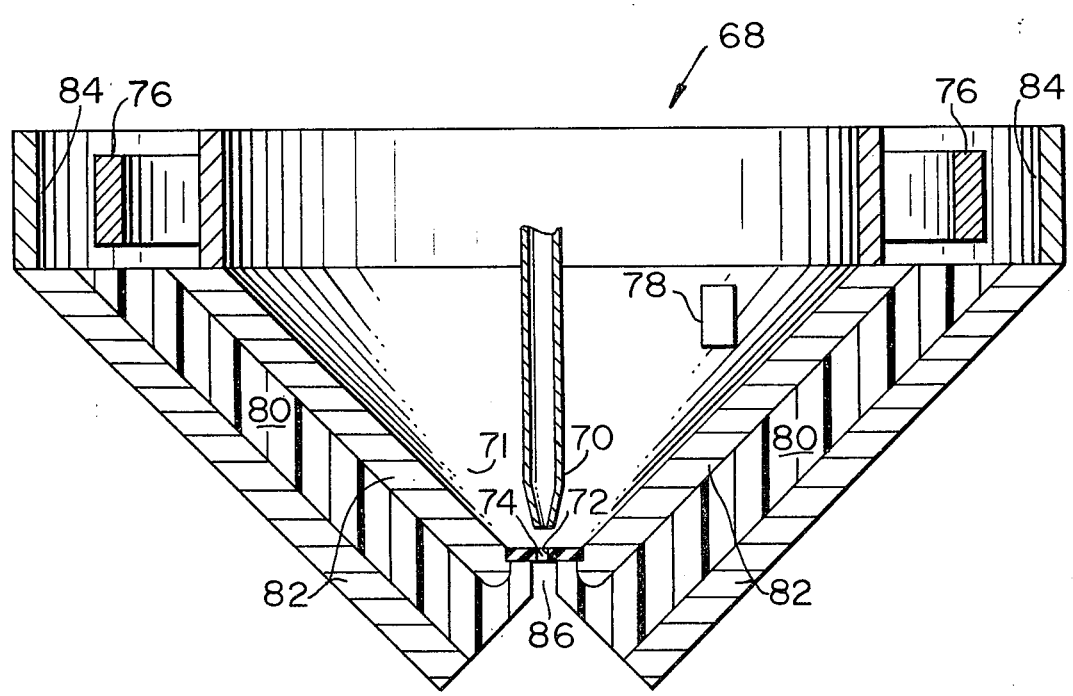
FIG-4-

USE OF FLUID RETARDING ION CONDUCTING MATERIAL

BACKGROUND OF THE INVENTION

1. Field of the Invention

The present invention relates to the use of fluid retarding, ion conducting material used to isolate electrolyte products from the region of electronic sensing of particles.

2. Discussion of the Prior Art

Various impedance or phase based particle sensing devices exist in the prior art for studying the physical properties of microscopic particles, such as biological cells carried in a liquid suspension, as illustrated by the pioneer U.S. Pat. No. 2,656,508, "Means for Counting Particles Suspended in a Fluid" W. H. Coulter, Oct. 20, 1953; and U.S. Pat. No. 4,014,611, "Aperture Module for Use in Particle Testing Apparatus", Simpson et al., Mar. 29, 1977. A well known "Coulter principle" of operation is referred to with particularity in these patents. Generally, these Coulter devices include two fluid vessels or chambers, each containing a conductive electrolyte solution. At least two electrodes having opposite polarity are immersed in the electrolyte solution, with each fluid compartment having one of the electrodes disposed therein. A sample of the electrolyte solution, having the particles suspended therein, is passed through a constricted fluid path or orifice interposed between the two fluid compartments. Although this constricted path can take different forms, in each device such path defines a sensing zone wherein the presence or absence of a particle in the constricted path gives rise to a detectable change in electrical characteristics of the path. For example, relatively poorly conductive biological cells passing through this constricted path displace a volume of electrolyte solution equal to the cell volume, causing a voltage drop by increasing the path impedance. To put it another way, the resistance between the two electrodes which are separated by the constricted path is increased by the cell presence. The resistance pulses defined by the voltage drops are used for particle counting and particle volume determination.

Modification of the above described prior art sensing scheme has led to the development of particle sorters, wherein the selective resistance pulses provided by constricted path activates the sorter to charge individually isolated droplets containing the activating cells. The charged droplets are deflected from the main stream by a static electric field into a collecting vessel. Typically, the prior art sorters include a first and a second sheath flow, with the second sheath flow being introduced below the orifice. A downstream return electrode is mounted in the second sheath. Consequently, the downstream particles are exposed to undesirable electrode products produced by the return electrode. An illustrative particle sorter has been sold by Coulter Electronics, Inc. of Hialeah, Florida.

In order to sense the impedance changes, it is necessary to have a current flow between at least two electrodes in the case of DC currents. The current flow is due to ions which proceed toward the oppositely charged electrode. However, there are several inherent problems brought about by this electrolysis process, which next will be discussed.

Almost all electrolyte solutions create unwanted gas at the electrodes. For instance, the electrolyte sodium chloride in solution (saline solution) forms oxygen, chlorine and hydrogen gases which take the form of gas bubbles, such bubbles frequently create noise in the impedance sensing device as such bubbles travel through the constricted path. At the same time, other undesirable electrolyte products are produced. For example, in the case of sodium chloride, hypochlorite is formed by the chlorine gas acting with the water, and can kill or damage biological cells.

Electrolysis normally changes the pH of the solution, such as where hydrogen ions form hydrogen and thereby make the solution more basic. Cells generally are viable only in a specific pH range, and such pH changes can even kill the cells. Moreover, the user may be operating the impedance sensing device based on assumed cell environment conditions. However, a change in pH, and therefore a change in cell environment, can lead to different physical properties of the cell, such as changes in the cell membrane. These different physical properties can lead to a change in cell volume; hence, a change in the detected resistance. Moreover, the electrodes can be fouled by the presence of various substances, including proteins.

Accordingly, it readily can be seen that there has been a long recognized need in the art of cytology to prevent the electrolyte products from interfering with the impedance sensing device and sorting processes.

In the case of simple impedance based cell sorters, such as the previously cited sorter, or more simply where the cells are to be collected, it is necessary to minimize the volume of liquid beneath the orifice. First, this minimized volume is desirable for the purpose of providing fidelity of collection, and secondly, not impeding fluid flow. Since the power electrodes must be of a finite size, it is necessary to position the downstream electrode remotely from the orifice.

The use of frits, gels and membranes in chemical art areas is well known. For instance, electrophoresis involves the movement of charged, dispersed particles in a colloidal system toward electrodes that have opposite charges, such process normally being used to separate molecular species, such as proteins which differ by charge or charge and shape. In order to separate properly the molecular species, it is desirable not to have bubbles which create fluid turbulences and changes in pH, which effect the mobility (velocity) of the species being separated. In short, a constant chemical composition of the solution employed to perform these separating tests is required. Consequently, fruits and other such means are used to separate the volume holding the electrodes from the volume in which separation occurs. However, there is no electronic sensing of individual particles in the electrophoresis process.

In prior art pH and other ion sensing meters, frits, gels and like means are used to protect and separate and maintain the precisely defined chemical milieu that is disposed around the internal electrode of the reference electrode from the solution being measured by the pH meter. However, in that there is a minimal amount of current in the pH meters, electrolyte products are of negligible consequence. The current in a pH meter is of the order of one billionith of that in a standard particle sensing transducer. Other chemical apparatuses, such as polargraphs and electrolylic half cells, use various conducting gels and frits. However, none of these processes involve impedance sensing of particles.

SUMMARY OF THE INVENTION

The present invention relates to an improved particle sensing transducer apparatus and method for studying the physical properties of particles suspended in an electrolyte solution. The sensing transducer is of the type using the "Coulter principle" of operation, wherein there is provided an orifice which forms a constricted path for a sample flow of electrolyte solution having a quantity of the particles suspended therein. The orifice also defines a constricted electrical path for an ionic current provided by a pair of electrodes, such electrodes being fluidly disposed on opposite sides of the orifice. The improvement comprises interposing a fluid retarding, ion conducting material between at least one of the pair of electrodes and the sample flow, thereby substantially isolating the sample flow from disruptive and harmful electrolyte products. These electrolyte products can include gas bubbles, which are formed at the electrode disposed upstream with respect to the orifice, that can pass through the orifice and produce inaccurate impedance readings. Also, these electrolyte products may include various noxious substances generated by the electrodes which damage the particles. Depending upon the application for which the sensing transducer apparatus is used, the present invention contemplates protecting the sample flow from the noxious substances produced by the electrode disposed either downstream or upstream with respect to the orifice, or by both electrodes. Moreover, the downstream use of a fluid retarding, ion conducting material allows for the minimizing of the volume of liquid beneath the orifice, and thereby is advantageous in those applications wherein the particles are to be collected.

BRIEF DESCRIPTION OF THE DRAWINGS

Further objects and advantages of the present invention will become apparent as the following description proceeds, taken in conjunction with the accompanying drawings in which:

FIG. 3 is a cross-sectional, diagramatic view of another embodiment of the improved sensing transducer apparatus which performs downstream activities on particles.

FIG. 4 is a cross-sectional view of a select portion of a sensing transducer apparatus which has a downstream sorting activity.

DETAILED DESCRIPTION OF THE PREFERRED EMBODIMENTS

Figure 1:
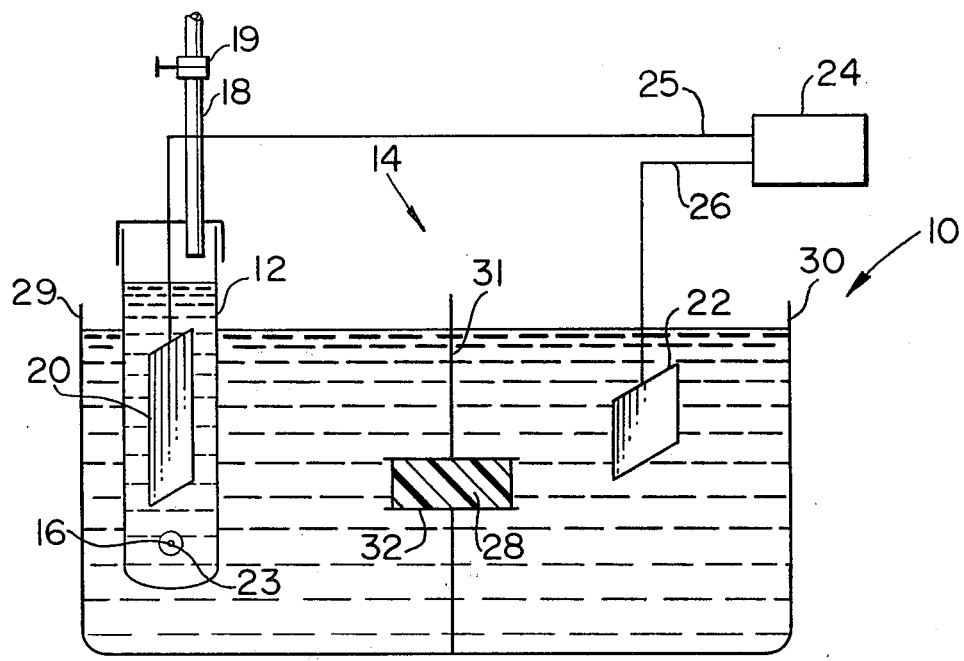
FIG. 1 is a diagramatic view of one embodiment of the improved sensing transducer apparatus.

A particle sensing transducer, generally identified as 10, is illustrated in FIG. 1. There is provided a first chamber 12 in the form of a tube which holds an electrolyte solution. A second chamber 14 is arranged with the first chamber 12 positioned therein; and the second chamber 14 also is provided with a quantity of electrolyte solution. Near the bottom of the first chamber 12 and in its side wall there is provided an orifice 16. The electrolyte solution is caused to flow from the second chamber 14 through the orifice 16 and into the first chamber 12 by virtue of an external vacuum source 18 (partially shown). A dilute suspension of particles, such as biological cells, is contained in the electrolyte solution of the second chamber 14. A stopcock 19 is opened and the external vacuum source 18 initiates a sample flow of electrolyte solution, having a quantity of the particles suspended therein, through the orifice. The sample flow is defined as that fluid which passes through the orifice. A pair of electrodes, a first electrode 20 and a second electrode 22, is immersed in the electrolyte solution. More specifically, the first electrode 20 is inserted in the first chamber 12 and the second electrode is inserted in the second chamber 14. By virtue of ion conduction, an electrical current is arranged to flow between the electrodes through the orifice 16, so that the presence of a particle in the orifice 16 causes a change in current flow. The orifice 16 forms a constricted electrical path which defines a sensing zone 23 for the detection of impedance changes caused by the particles. The electrodes 20 and 22 are attached to a detecting device 24 by leads 25 and 26.

The above described transducer structure is well known in the art and can take many different conventional forms, all of which can make use of the invention to be described hereinafter. In general, these particle sensing transducers of the prior art have two electrolyte chambers, such as the first chamber 12 and second chamber 14, which are interconnected by a constricted fluid path, such as the orifice 16. Particles are introduced into one of the chambers and a sample flow having the particles suspended therein is drawn through the constricted path into the other chamber. The specific structure of this arrangement per se forms no part of the present invention.

It should also be appreciated that in the prior art impedance sensing transducers, the second electrode 22 would have been inserted directly into the second chamber 14. Consequently, the particles would be exposed to the previously described harmful electrolyte products prior to their passage through the orifice 16. Moreover, gas bubbles formed at the second electrode 22 could pass with the sample flow through the orifice 16 and create the previously described, inaccurate impedance readings.

The embodiment of the present invention illustrated in FIG. 1 contemplates isolating the second electrode 22 from the sample flow by use of a filter means in the form of a gel 28, which is interposed between the second electrode 22 and the orifice 16. This is contrary to the prior art practice which would normally involve inserting the electrode 22 into the chamber containing the particles. More specifically, one way to implement this separation is to divide the second chamber 14 into two compartments 29 and 30, each of which holds a quantity of the electrolyte solution. This can be accomplished by the insertion of a dividing wall 31 into the second chamber 14 as illustrated in FIG. 1, or by other obvious adaptations, such as having two spaced-apart compartments. In compartment 29, the sample flow, having the particles, is moved to the orifice 16; whereas, the compartment 30 has the second electrode 22 disposed therein. The compartment 29 is connected electrically to the compartment 30 by means of a passageway 32, such passageway encasing the gel 28. By virtue of this arrangement, ion conduction can proceed between the electrodes 20 and 22 by passing through the gel 28. On the other hand, fluid flow from the compartment 30 is retarded by the gel 28. By virtue of this electrical conduction, fluid retarding relationship, the particles in the compartment 29 are not exposed to noxious electrode products produced at the second electrode 22, such as chlorine gas, hypochlorite, and changes in pH, prior to their passing through the orifice 16. Moreover, bubbles formed at the second electrode 22 do not pass through the gel 28 and therefore do not pass through the orifice 16. Since the sample flow proceeds into the first chamber 12, bubbles and electrolyte products produced at the first electrode 20 do not normally affect the particles until after they enter the first chamber 12 and pass through the sensing zone 23 of the orifice 16. Moreover, the fluid flow through the orifice 16 prevents any bubbles formed at the first electrode 20 from entering the sensing zone 23 of the orifice 16.

Figure 2:
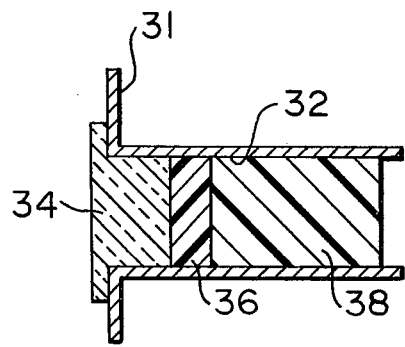
FIG. 2 is an enlarged fragmentary view of a modified passageway of the sensing transducer apparatus shown in FIG. 1.

It should be appreciated that materials and means other than gel 28 can be used for the filter means to provide an electrical impedance which is relatively small, while retarding or stopping the fluid flow. For example, as illustrated in FIG. 2, a frit or a membrane or like materials can be used in place of or in addition to the gel 28 and is arranged on the assumption that the hydrostatic force is exerted into the frit containing end of the passageway 32. Such materials can be used singly or in combination. More specifically, gels are less permeable to fluid, while frits provide more structural support, but generally are more permeable to fluid. Where there is a substantial hydrostatic pressure, it may be desirable to use the frit 34 and the gel 36. Moreover, as shown in the embodiment of FIG. 2, if the hydrostatic pressure is great enough, it may be desirable to use two types of gels. The first type of gel preferably should be rigid, such as a cross-linked gel 36, which is located next to the frit 34, and the second gel is a conventional gel 38. The cross-linked gel 36 is more resistant to deterioration under hydrostatic pressure and thus can act as a plug to stop the conventional gel from being pushed through the frit 34. Generally, the conventional gel has a somewhat faster diffusion rate for the ions than the cross-linked gel, but the cross-linked gel provides more resistance against hydrostatic pressure. In FIG. 1, only the gel 28, possibly an agar gel, is shown in the passageway 32. The use of only the gel 28 is sufficient in such an application as that illustrated in FIG. 1 in that there is practically no hydrostatic pressure. However, as illustrated in FIG. 2, frit 34 and/or a combination of the cross-linked gel 36 and conventional gel 38 can be included where significant hydrostatic pressures exist. The cross-linked gel 36 can be a commercially available gel which is cross-linked, for example by glutaraldehyde fixation, a well known cross-linking agent, to immobilize the same within the passageway 32. By virtue of this arrangement, the molecules of the cross-linked gel 36 are formed into a three dimensional matrix which is sufficiently rigid to prevent the hydrostatic pressure from pushing the conventional gel through the porous frit 34. It should be understood that frits and gels are merely used as illustrative examples and that any material, such as ultrafiltration membranes commercially available from Amnicon Corp. of Lexington, Massachusetts, which sufficiently retards fluid flow while allowing ion flow is within the scope of this invention. A membrane which could be useful in this implementation is a thin substrate that impedes the flow of fluid, yet permits the flow of ions, such as a thin gel pulled taut over a supporting structure. Also, such flow retarding materials do not have to stop all of the fluid flow, in that some fluid flow through the flow retarding material may be acceptable for a particular application.

Another possible application of the fluid retarding, ion conducting material can be understood by initially referring back to FIG. 1. As previously described, the particles are not exposed to the electrolyte products from the second electrode 22 before passing through the sensing zone 23. As shown in FIG. 1, the particles would, after passing through the sensing zone 23, be exposed to electrolyte products from the first electrode 20. It may be desirable to collect viable cells and/or avoid undesirable buildup of electrolyte products on the first electrode 20. To avoid these undesirable features of electrolysis, the first electrode 20 also can be fluidly isolated by a gel or like means in a manner similar to that of the second electrode 22. Such an implementation is illustrated in FIG. 3.

Referring to the cross-sectional view of FIG. 3, a particle sensing transducer 10 is illustrated with a first and a second chamber 12 and 14, respectively, such chambers being electrically interconnected through an orifice 44. The upstream second chamber 14 is divided into two electrolyte containing compartments, a first compartment 46 having a first electrode 48 disposed therein and a second compartment 50 which is in fluid communication with the orifice 44. The first compartment 46 is electrically connected to the second compartment 50 by frit 52 and gel 54. The downstream first chamber 12 also is divided into two electrolyte containing compartments, a third compartment 56 having a second electrode 58 therein and fourth compartment 60, which is in fluid communication with the orifice 44. The second electrode 58 preferably has a large surface area and can have, for instance, a circular configuration. The fourth compartment 60 is configured and dimensioned to receive a sample flow having the particles suspended therein, which passes from the second compartment 50, through the orifice 44, and into the fourth compartment 60. The third compartment 56 and the fourth compartment 60 are electrically connected through a gel 62 and a cylindrically-shaped frit 64. By virtue of this arrangement, close electrical contact can be made with the downstream fluid area, the fourth compartmer 60, while preventing the electrode products from invading such area.

Various well known downstream activities can occur with the above described structure of FIG. 3. For instance, particle sorting may be performed or, alternatively, the close electrical contact of the gel 62 and frit 64 can be part of an electrical arm in a bridge circuit. The embodiment of FIG. 3 is intended to be generic in concept of all conventional particle sensing transducers, wherein downstream activities occur after the sample flow passes through the orifice 44. In these conventional transducers, it is desirable to minimize the length of fluid travel of the particles past the orifice 44. For example, the ability for particle sorting may be diminished or lost after a lengthy downstream fluid flow by the pressure of the fluid, delay in sorting, and jitter problems caused by the fluid flow. These problems can be decreased by the positioning of a downstream electrode immediately below the orifice 44. Although this reduces the fluid travel, as a practical matter, it results in the surface area of such electrode being minimized. A small surface area for the electrode in turn causes a new set of problems in the form of noise generated and overvoltage problems being maximized. The prior art has not been able to solve this dilemma and has resorted to using a second sheath for remotely disposing a large electrode. Although this allows for a large downstream electrode, the inclusion of the second sheath causes turbulances in the downstream fluid flow, so as to make control of particle positioning in the stream more difficult. Also, the second sheath uses large quantities of liquid, which is expensive.

In FIG. 3, an access channel 66 provides for a relatively small electrical contact area with the downstream area of the fourth compartment 60, thereby minimizing the length of the downstream fluid flow. Additionally, the access channel 66 provides for the remote disposition of the electrode 58. Hence, a sizable electrode surface may be provided which minimizes noise and overvoltage, without the use of the second sheath and its associated problems.

A specific application of the fluid retarding, ion conducting material to a conventional particle sorting transducer 68, sold by Coulter Electronics, Inc. of Hialeah, Florida and identified in the Background Section, is illustrated in FIG. 4. The particle sorter itself is of conventional design and, for that reason, only the part which is modified by the present invention is illustrated in FIG. 4. More specifically, the conventional particle sorter normally comprises a sample flow of suspended particles which are ejected through a capillary 70. This sample flow is surrounded by a sheath flow and proceeds through the orifice 72. In this well known type of system, the sample flow or sample stream comprises a suspension fluid containing the particles, which flows down the capillary 70. This sample flow is entrained by the sheath flow comprising sheath fluid (usually saline) which flows down the annular region between the capillary 70 and an inner wall 71. The combined flows laminarly proceed down to and through the orifice 72. The orifice 72 defines a sensing zone 74 for receiving the flow sample. A pair of power electrodes, first and second electrodes 76 and 78, are in electrical communication with opposite sides of the orifice 72 so as to provide for an ionic current through the orifice 72. In practice, more electrodes can be involved in the detection of the particles. After proceeding through the sensing zone 74, liquid droplets containing particles are formed from the sample flow, which is in the form of a liquid jet, by applying to it small mechanical disturbances with ultrasonic frequencies. Thus, impedance sensing occurs, then a plurality of droplets are formed. Droplets containing cells to be sorted are charged and deflected from the main stream by a static electric field into a collecting vessel, in one implementation. All of this structure of the cell sorter is well known in the art.

In the conventional particle sorting transducer of the prior art, as illustrated by the one identified in the Background Section, a second sheath flow is positioned below the orifice 72. Normally, a downstream electrode is positioned in the extremity regions of the second sheath. The electrode is normally held at ground potential to prevent the droplet charging pulses from entering the sensing zone 74. Referring to FIG. 4, this basic prior art scheme is modified by the present invention by eliminating the second sheath flow of the prior art and substituting therefor a gel 80 within a passageway 82. In this manner, electrical contact is made through the gel 80 or like material, instead of through the second sheath flow; while the first electrode 76 is isolated fluidly from the sample flow. In that a power electrode, such as first electrode 76, requires an electrolyte solution to carry out the electrolysis process, the second electrode 78 is immersed in electrolyte solution contained in a fluid container 84. As with the other applications of a fluid retarding, ion conducting material heretofor described, frits (not shown) could be incorporated into the design for added mechanical strength, such frits being located in the passageway 82 to retain the gel 80 against a hydrostatic force.

In sorting cells, it is particularily important that the cells are not damaged by the electrolyte products; and, in some cases, it is desirable to have viable cells after sorting. Hence, not only is it necessary to prevent exposure of the cells to harmful electrolyte products before passing through the sensing zone 74, but exposure after passing through the sensing zone 74 must be avoided. Therefore, as illustrated in FIG. 4, the sample flow that has passed through the sensing zone 74 is protected from electrolyte products generated by the first electrode 76. With the second sheath of the prior art design, there was no such protection. Moreover, electrolyte solution can be expensive and, with the prior art design, large amounts of electrolyte solution were required to maintain the second sheath flow.

It now can be appreciated that the same structural features of the invention exist in the embodiments of FIGS. 1, 3 and 4, even though the embodiment of FIG. 4 has been modified to a sheath flow system which is coupled into a particle cell sorting system. More specifically, a first chamber for electrolyte solution is disposed downstream relative to the orifice 72 and would include a liquid jet receiving area, generally indicated as 86, the passageway 82, and the container 84. Consequently, this first chamber comprises the receiving area 86 which defines a first fluid compartment; and the container 84 which defines a second fluid compartment; with the first and second fluid compartments being separated by the gel filled passageway 82. The first fluid compartment is in fluid communication with the orifice 72; while, the second fluid compartment has the first electrode 76 disposed therein. A second chamber is disposed upstream with respect to the orifice 72 and has the second electrode 78 mounted therein and encompasses the sheath flow.

In summary, it can be seen that there is a need for preventing exposure of particles to electrolyte products prior to passing the particles through an impedance sensing zone. As shown in FIG. 1, the electrolyte products from the upstream electrode (relative to orifice 16), the first electrode 20, are blocked substantially by the gel 28 from coming into contact with the particles. This also prevents bubbles from entering the sensing zone 23. It also can be seen that in some applications, such as cell sorting, or any other means of cell collection, there is a need for preventing exposure of particles to electrolyte products after the particles pass through the sensing zone. As illustrated in FIG. 4, the electrolyte products from the downstream electrode 76 (relative to orifice 72) are blocked substantially by the gel 80 from coming into contact with the particles. Yet, in both embodiments of FIGS. 1 and 4, the gel 28 or 80 allows for the flow of ionic current. The use of the gel permits the downstream electrode to be remotely disposed frm the downstream flow and thus permits the geometry of this region to be optimized for cell sorting or other means of cell collection.

Yet another application of the present invention is to utilize the fluid retarding, ion conducting material in a conventional particle sensing transducer, having a conventional bridge circuit (not shown), for measuring impedance in the sensing zone. An illustrative bridge circuit is disclosed in two articles in "The Journal of Histochemistry and Cytochemistry", by the Histochemical Society, Inc. The first article appears in Volume 22, No. 7, pp. 626–641, 1974 and is entitled "Computer-Based Electronic Cell Volume Analysis with AMAC II Transducer" and the other article appears in Volume 1, January, 1978 and is entitled "The AMAC IIA, A True Bridge Circuit Coulter-Type Electronic Cell Volume Transducer". It should be understood that the specific structure of the bridge circuit is not part of the present invention. These conventional bridge circuits normally have a series of connecting channels comprising small holes which connect the downstream sample flow with a displacement rheostat and a remote downstream power electrode. In addition to the previously described problems with downstream power electrodes, this bridge arrangement creates an additional problem if a fluid flow is used as the conductive element in these connecting channels. This fluid flow, when proceeding through the small channels, creates noise that interferes with the particle sensing. The replacement of this fluid flow with a fluid retarding, ion conducting material, such as various combinations of frits and gels, eliminates this source of noise.

Although particular embodiments of the invention have been shown and described here, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle sensing transducer apparatus for detecting the physical properties of particles suspended in an electrolyte solution, wherein said transducer apparatus includes first chamber means containing a first electrode disposed in a quantity of the electrolyte solution, second chamber means containing a second electrode disposed in a quantity of the electrolyte solution, orifice means for establishing a constricted electrical path between the electrodes by providing a passageway between the chamber means for a sample flow of the electrolyte solution having the particles suspended therein, wherein the improvement comprises:
    filter means interposed in fluid retarding, ion conducting relationship between the orifice and at least one of the electrodes for providing an ionic current flow but retarding a fluid flow from the electrode, whereby said filter means substantially isolates the sample flow from at least one of the electrodes.

2. In the transducer apparatus of claim 1,
    said filter means being interposed between the first electrode and the orifice within the first chamber.
3. In the transducer apparatus of claim 1,
    said filter means being interposed between the second electrode and the orifice within the second chamber.
4. In the transducer apparatus of claim 1,
    said filter means being interposed between the first electrode and the orifice within the first chamber and between the second electrode and the orifice within the second chamber.
5. In the transducer apparatus of claim 1,
    said filter means defining a pair of electrolyte solution compartments within at least one of the chambers, one of said compartments having the electrode of the chamber therein and the other said compartment disposed in fluid communication with the other chamber through the orifice means,
    said filter means including a passageway between said pair of compartments, said passageway having disposed therein a fluid retarding, ion conducting material.
6. In the transducer apparatus of claim 1,
    said filter means including a frit.
7. In the transducer apparatus of claim 1,
    said filter means including a membrane.
8. In the transducer apparatus of claim 1,
    said filter means including a constricted passageway for encasing a fluid retarding, ion conducting material.
9. In the transducer apparatus of claim 1,
    said filter means including a gel.
10. In the transducer apparatus of claim 9,
    at least a portion of said gel comprising a cross-linked gel.
11. In the transducer apparatus of claim 10,
    said filter means further including a frit.
12. In the transducer apparatus of claim 10,
    a remaining portion of said gel comprising a conventional gel.
13. In the transducer apparatus of claim 12,
    said cross-linked gel being disposed between said frit and said conventional gel whereby said frit provides mechanical support and said cross-linked gel prevents said conventional gel from passing through said frit when there is a sufficient hydrostatic force.
14. A method of studying the physical properties of particles suspended in an electrolyte solution, comprising the steps of:
    passing a sample flow of electrolyte solution through a constricted electrical path from a first chamber having an upstream first electrode into a second chamber having a downstream second electrode,
    conducting an ionic current between the electrodes so as to pass the current only through the constricted electrical path,
    retarding a fluid flow of the electrolyte solution between the sample flow and at least one of the electrodes.
15. In the method of claim 14,
    said step of retarding the fluid flow comprising retarding the fluid flow between the upstream first electrode and the sample flow.
16. In the method of claim 14,
    said step of retarding the fluid flow comprising retarding the fluid flow between the downstream second electrode and the sample flow.
17. In a particle sensing transducer for detecting the physical properties of particles in accordance with the Coulter principle of particle sensing; in which orifice means, through which the particles move in a flow of electrolyte, is interposed between electrode means, the improvement comprising:
    means for substantially isolating the flow of electrolyte containing the particles from at least a portion of said electrode means, while providing for an ion conducting relationship between said orifice and at least a portion of said electrode means.
18. In the transducer of claim 17,
    said electrode means including at least two spaced apart electrodes; and
    said flow isolating means including fluid retarding filter means positioned between said orifice means and at least one of said electrodes.

* * * * *